US009433638B1

(12) United States Patent
Puleo et al.

(10) Patent No.: US 9,433,638 B1
(45) Date of Patent: Sep. 6, 2016

(54) POLYMERIC PRODRUG

(71) Applicant: University of Kentucky Research Foundation, Lexington, KY (US)

(72) Inventors: David Puleo, Lexington, KY (US); Thomas Dziubla, Lexington, KY (US); Theodora Asafo-Adjei, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 147 days.

(21) Appl. No.: 14/505,381

(22) Filed: Oct. 2, 2014

Related U.S. Application Data

(60) Provisional application No. 61/885,915, filed on Oct. 2, 2013.

(51) Int. Cl.
*A61K 31/765* (2006.01)
*A61K 31/366* (2006.01)

(52) U.S. Cl.
CPC ........... *A61K 31/765* (2013.01); *A61K 31/366* (2013.01)

(58) Field of Classification Search
CPC .......................... A61K 31/765; A61K 31/366
See application file for complete search history.

(56) References Cited

U.S. PATENT DOCUMENTS

| 5,882,682 | A | 3/1999 | Rork et al. |
| 6,569,461 | B1 | 5/2003 | Tillyer et al. |
| 8,071,692 | B2 | 12/2011 | Zhao |
| 2003/0195610 | A1 | 10/2003 | Herrmann et al. |
| 2005/0239884 | A1 | 10/2005 | Meyer et al. |
| 2007/0265457 | A1 | 11/2007 | Singh et al. |
| 2008/0213378 | A1 | 9/2008 | Cooper et al. |
| 2010/0086602 | A1 | 4/2010 | Egashira |
| 2010/0119582 | A1 | 5/2010 | Boerger et al. |
| 2012/0310366 | A1 | 12/2012 | Li et al. |

FOREIGN PATENT DOCUMENTS

| CN | 101613284 | * 12/2009 | .............. A61P 29/00 |
| WO | 2008057048 | 5/2008 | |

OTHER PUBLICATIONS

Chen et al, English Machine Translation of CN101613284, Translated Jun. 6, 2016, pp. 1-35.*
Chang, K.Y. and Lee, Y.D. (2009). Ring-opening polymerization of epsilon-caprolactone initiated by the antitumor agent doxifluridine, Acta Biomater 5:1075-1081.
Erdmann, L., Macedo, B., and Uhrich, K.E. (2000). Degradable poly(anhydride ester) implants: effects of localized salicylic acid release on bone, Biomaterials 21:2507-2512.
(Continued)

*Primary Examiner* — Trevor Love
(74) *Attorney, Agent, or Firm* — Stites & Harbison PLLC; Terry L. Wright

(57) ABSTRACT

The presently-disclosed subject matter includes compounds that comprise an initiator and an active agent that is covalently bonded to the initiator through a ring-opening polymerization process, an atom-transfer radical polymerization process, a Michael addition reaction, or a ring-opening metathesis polymerization process. In some embodiments the active agent includes simvastatin. The presently-disclosed subject matter also includes methods for making the compositions and methods for using the compositions to treat tissue wounds.

10 Claims, 9 Drawing Sheets

(56) References Cited

OTHER PUBLICATIONS

Erdmann, L. and Uhrich, K.E. (2000). Synthesis and degradation characteristics of salicylic acid-derived poly (anhydride-esters), Biomaterials 21:1941-1946.

Schmeltzer, R.C. and Uhrich, K.E. (2006). Synthesis and characterization of antiseptic-based poly(anhydride-esters), Polymer Bulletin 57:281-291.

Rosario-Melendez, R., Harris, C.L., Delgado-Rivera, R., Yu, L., and Uhrich, K.E. (2012). PolyMorphine: an innovative biodegradable polymer drug for extended pain relief, J Control Release 162:538-544.

Mundy, G., Garrett, R., Harris, S., Chan, J., Chen, D., Rossini, G., Boyce, B., Zhao, M., and Gutierrez, G. (1999). Stimulation of bone formation in vitro and in rodents by statins, Science 286:1946-1949.

Garrett, I.R., Gutierrez, G., and Mundy, G.R. (2001). Statins and bone formation, Curr. Pharm. Des. 7:715-736.

Grasser, W.A., Baumann, A.P., Petras, S.F., Harwood, H.J., Jr., Devalaraja, R., Renkiewicz, R., Baragi, V., Thompson, D.D., and Paraklar, V.M. (2003). Regulation of osteoclast differentiation by statins, J. Musculoskelet. Neuronal Interact. 3:53-62.

Staal, A., Frith, J.C., French, M.H., Swartz, J., Gungor, T., Harrity, T.W., Tamasi, J., Rogers, M.J., and Feyen, J.H. (2003). The ability of statins to inhibit bone resorption is directly related to their inhibitory effect on HMG-CoA reductase activity, J. Bone Miner. Res. 18:88-96.

Diomede, L., Albani, D., Sottocorno, M., Donati, M.B., Bianchi, M., Fruscella, P., and Salmona, M. (2001). In vivo anti-inflammatory effect of statins is mediated by nonsterol mevalonate products, Arterioscler Thromb Vasc Biol 21:1327-1332.

Adam, O. and Laufs, U. (2008). Antioxidative effects of statins, Arch Toxicol 82:885-892.

Mermis, J.D. and Simpson, S.Q. (2012). HMG-CoA Reductase Inhibitors for Prevention and Treatment of Severe Sepsis, Curr Infect Dis Rep 14:484-492.

Bjorkhem-Bergman, L., Ekstrom, L, and Eriksson, L.C. (2012). Review: Exploring anticarcinogenic agents in a rat hepatocarcinogenesis model—focus on selenium and statins, In Vivo 26:527-535.

Labet, M. and Thielemans, W. (2009). Synthesis of polycaprolactone: a review, Chem Soc Rev 38:3484-3504.

Storey, R.F. and Sherman, J.W. (2002). Kinetics and mechanism of the stannous octoate-catalyzed bulk polymerization of epsilon-caprolactone, Macromolecules 35:1504-1512.

Kricheldorf, H.R., Kreisersaunders, I., and Boettcher, C. (1995). Polylactones .31. Sn(li)Octoate-Initiated Polymerization of L-Lactide—a Mechanistic Study, Polymer 36:1253-1259.

Wattamwar, P.P., Biswal, D., Cochran, D.B., Lyvers, A.C., Eitel, R.E., Anderson, K.W., Hilt, J.Z., and Dziubla, T.D. (2012). Synthesis and characterization of poly(antioxidant beta-amino esters) for controlled release of polyphenolic antioxidants, Acta Biomater 8:2529-2537.

Wattamwar, P.P., Hardas, S.S., Butterfield, D.A., Anderson, K.W., and Dziubla, T.D. (2011). Tuning of the pro-oxidant and antioxidant activity of trolox through the controlled release from biodegradable poly(trolox ester) polymers, J Biomed Mater Res A 99:184-191.

Jeon, J.H., Piepgrass, W.T., Lin, Y.L., Thomas, M.V., and Puleo, D.A. (2008). Localized intermittent delivery of simvastatin hydroxyacid stimulates bone formation in rats, J Periodontol 79:1457-1464.

Ikada, Y. and Tsuji, H. (2000). Biodegradable polyesters for medical and ecological applications, Macromol. Rapid Commun. 21:117-132.

Banerjee SS, Poly(ethylene glycol)—Prodrug Conjugates:Concept, Design, and Applications, Journal of Drug Delivery 2012.

Carbone AL and Uhrich KE, Design and Synthesis of Fast-Degrading Poly(anhydride-esters), Macrornol Rapid Commun (30) 2009: 1021-1026.

Gross RA Ganesh M., and Lu W, Enzyme catalysis breathes new life into polyester condensation polymerizations, Trends in Biotechnology (28)2010, 435-443.

Dhandayuthapani B et al., Polymeric Scaffolds in Tissue Engineering Application: A Review, International Journal of Polymer Science (2011) 2011, 1-19.

Kohane, et al., Polymeric Biomaterials in Tissue Engineering; Pediatric Research; 2008; vol. 63, No. 5, pp. 487-491.

\* cited by examiner

POLYMERIC PRODRUG

RELATED APPLICATIONS

This Application claims the benefit of U.S. Provisional Patent Application No. 61/885,915, filed Oct. 2, 2013, the entire disclosure of which is hereby incorporated by reference.

GOVERNMENT SUPPORT

This invention was made with government support under grant number DGE-0653710 awarded by National Science Foundation (NSF). The government has certain rights in the invention.

TECHNICAL FIELD

The present invention generally relates to polymeric prodrugs. In particular, certain embodiments of the present invention relate to polymer compounds that degrade to release an active agent.

BACKGROUND

The need to treat bone defects resulting from age-related degenerative disease, trauma, and reconstructive surgery continues to grow at a significant rate. An estimated 2.2 million bone grafting procedures are performed annually worldwide at a cost of $2.5 billion. Considering the "graying" of the U.S. population, in which the percentage of persons 55 years and older is expected to nearly double over the next 30 years, tremendous societal impact is inevitable. Consequently, the market for orthopedic biomaterials will continue to expand.

Autologous (i.e., autografts) and cadaveric (i.e., allografts) bone are the most commonly used grafting materials to treat bone defects. Each, however, has drawbacks related to morbidity associated with a second surgical procedure for autografts and the potential for disease transmission with allografts. These observations have led to development of synthetic materials and tissue engineering approaches for use in bone regeneration. Bone graft substitutes have used materials of natural and synthetic origin. Ongoing developments focus on enhancing biological activity, such as by incorporating stem cells (e.g., mesenchymal stem cells) and growth factors (e.g., bone morphogenetic protein (BMP) 2) into bone graft substitute materials.

Synthetic biodegradable polymers are also used for drug delivery and to aid in tissue regeneration. Candidate materials include polyanhydrides, polyamides, polycarbonates, and polyorthoesters. The majority of resorbable synthetic polymers utilized for drug delivery and tissue engineering belong to the polyester family, such as poly(glycolic acid), poly(lactic acid), and poly(lactic-co-glycolic acid) (PLGA). These materials are relatively biocompatible, can degrade by the hydrolytic cleavage of ester bonds, and have degradation and mechanical properties that can be tailored by changing monomer ratio. Their degradation products of glycolic and lactic acid are metabolically removed from the body by conversion to carbon dioxide and water in the Krebs cycle. Other common polyesters include poly(ε-caprolactone), polyvalerolactone, polydioxanone, and their blends and copolymers.

Furthermore, although certain drugs are intended for systemic therapy, many are most effective if targeted to or placed within a specific site. To this end, drugs are routinely encapsulated in polymers. Entrapment in a solid matrix protects the molecules from environmental effects, and controlled release can be achieved. Persistent challenges, however, include instability of encapsulated drugs, incomplete release, and initial burst.

Therefore, since cells and tissues require exposure to bioactive agents at particular concentrations and doses for certain durations, limited release kinetics is a shortcoming of many drug delivery systems in regenerative medicine. Consequently, some have attempted to develop drugs conjugated to polymers to extend release duration. Among others, water soluble polymers, such as poly(ethylene glycol), polylysine, polyglutamic acid, and N-(2-hydroxypropyl)methacrylamide (HPMA) have been used for this purpose. With these systems, drugs are attached as pendants linked to the polymeric backbone via ester, amide, and hydrazone bonds. Depending on the spacer molecule chosen, drug release can be prolonged until cleavage in a desired environment, such as pH-sensitive release in a lysosome. Other applications include targeting to specific cells and prolonging circulation time by shielding the drug from degradative enzymes and preventing opsonization. The number of molecules (i.e., payload) that can be attached to the backbone, however, is limited by the number of functional groups required for conjugation.

Hence, there remains a need for degradable compositions and compounds for treating tissue wounds, including bone tissue wounds, that can release drugs at a wound site in a controlled manner. There also remains a need for such compositions and compounds whose payload is not limited by the number of functional groups present on a polymer backbone.

SUMMARY

The presently-disclosed subject matter meets some or all of the above-identified needs, as will become evident to those of ordinary skill in the art after a study of information provided in this document.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

In some implementations of the presently-disclosed subject matter, a compound is provided that comprises an initiator and an active agent that is covalently bonded to the initiator through a ring-opening polymerization process, an atom-transfer radical polymerization process, a Michael addition reaction, or a ring-opening metathesis polymerization process. In some implementations the initiator comprises one or more hydroxyl groups configured to react and bind to the active agent, and exemplary initiators can include methoxypoly(ethylene glycol) (mPEG). In some implementations the active agent includes a lactone group, and exemplary active agents include statins, such as simvastatin. In this regard, in some implementations the compounds include a molar ratio of the initiator to the active agent is about 1:1 to about 1:100.

In some implementations the compounds are a polymer that includes a linear or a branched structure. In some instances the compounds can include a molecular weight of about 500 Da to about 80 kDa. Exemplary compounds can further comprise a targeting agent that is selective for a target substance.

In some implementations the compound is a copolymer, and in specific embodiments the compound is a diblock copolymer. For instance, certain embodiments of the present compounds include the formula:

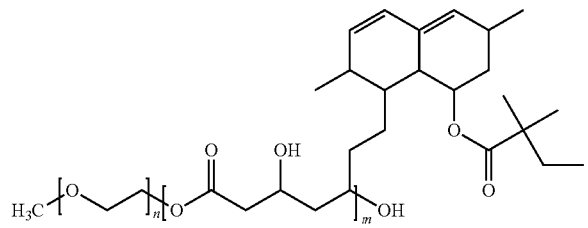

wherein n is about 1 to about 44 and m is about 1 to about 258.

The presently-disclosed subject matter also provides methods for making a compound. In some implementations the methods for making a compound include providing an initiator, mixing an active agent with the initiator to form a mixture, adding a catalyst to the mixture, and then reacting the mixture via a ring-opening polymerization process to form a compound that includes the initiator and the active agent. In some implementations the catalyst is selected from a metallic catalyst, an enzymatic catalyst, an organic catalyst, and combinations thereof.

Further still, the presently-disclosed subject matter provides methods for treating a wound in a subject with the presently-disclosed compounds. In some implementations, the methods for treating a wound comprise administering a composition to the wound of a subject, the composition including an initiator and an active agent that is covalently bonded to the initiator through a ring-opening polymerization. In some implementations the wound is a bone wound, a skin wound, or a combination thereof. Also, in some implementations the step of administering a composition includes contacting the wound with the composition.

Additional features and advantages of the present invention will also become evident to those of ordinary skill in the art after a study of the description, figures, and non-limiting examples in this document.

DESCRIPTION OF THE DRAWINGS

Illustrative aspects of embodiments of the present invention will be described in detail with reference to the following figures wherein.

DESCRIPTION OF EXEMPLARY EMBODIMENTS

Figure 1:
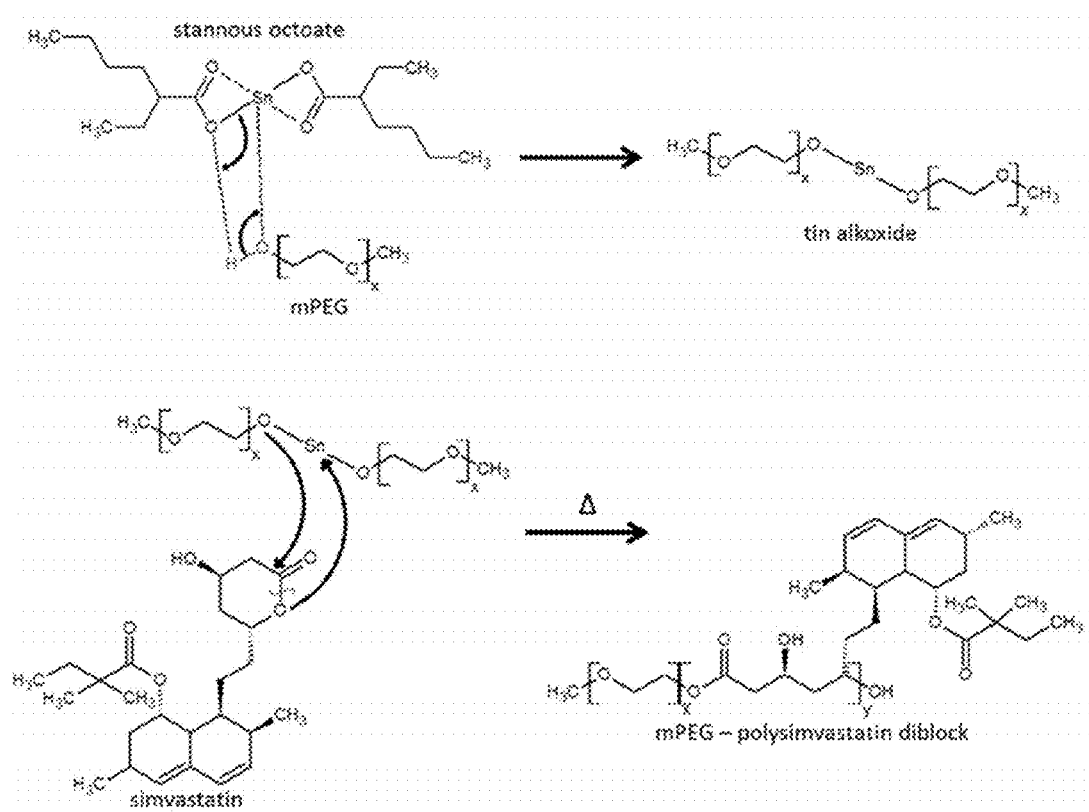
FIG. 1 includes a schematic diagram showing a ring-opening polymerization reaction between simvastatin and poly(ethylene glycol) methyl ether (mPEG) that yields a mPEG-poly(simvastatin) diblock.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding, and no unnecessary limitations are to be understood therefrom.

The presently-disclosed subject matter includes compounds that comprise polymeric prodrugs. More specifically, embodiments of the present compounds include an initiator and an active agent, wherein the active agent is covalently bonded to the initiator through a ring-opening polymerization process, an atom-transfer radical polymerization process, a Michael addition reaction, a ring-opening metathesis polymerization process, or a combination thereof.

The present inventors have conceived the present polymeric prodrugs to solve some of the long-felt problems associated with known polymeric drug compositions. Embodiments of the present compounds are formed via a ring-opening polymerization process to combine an initiator, an active agent, and, optionally, other substances. Embodiments of the compounds can thus form biodegradable compositions that degrade to release active forms of the active agents. The present compounds therefore differ from current polymeric drug formulations, which typically consist of drugs that are mixed with a polymeric material, encapsulated in a polymeric material, or are conjugated to a polymeric material via functional groups located along the polymer's backbone. Thus, while the present compounds are themselves comprised of active agents, currently known materials simply include a bioinert polymer that serves as an agent carrier.

In this regard, the mechanisms of polymer degradation and drug release of the present compounds can be the same since the chemical structure of the compound is comprised of the polymeric prodrug. In other words, since the active agent is directly incorporated into the present compounds, degradation of the compounds releases the active agent into the surrounding environment. Furthermore, polymerization of the prodrug (e.g., simvastatin) eliminates certain limitations on the number of prodrug molecules provided by the compounds relative to current polymer-prodrug systems. As a result, relatively increased concentrations of active agents can be provided in the present compounds, which can provide more efficient therapeutic effects and localized release of active agents.

In certain embodiments the presently-disclosed subject matter includes novel compounds and methods for making the same that include a biodegradable poly(ethylene glycol methyl ether-block-simvastatin) copolymer. Within a physiological environment, the copolymer can degrade by hydrolysis of ester bonds into the osteogenic biomolecules of simvastatin for therapeutic treatment.

The terms "biodegradable," "degradable," or the like are used interchangeably herein to refer to compounds and compositions that degrade under physiological conditions and/or are metabolized or excreted with little to no adverse effects to a subject. In certain embodiments, the compounds are metabolized or excreted without permanent damage to the subject. Biodegradable compounds can be hydrolytically degradable, can require cellular and/or enzymatic action to fully degrade, or both. Biodegradable compounds also include compounds that are broken down within cells. Degradation may occur by hydrolysis, oxidation, enzymatic processes, phagocytosis, or other processes. Degradation rates for compounds can vary, and may be on the order of hours, days, weeks, months, or years, depending on the embodiment of the compound. In some embodiments the compounds and compositions include prodrugs that can degrade to form active agents.

Additionally or alternatively, embodiments of the presently-disclosed compounds can be biocompatible. The term "biocompatible" as used herein describes a characteristic of compounds that do not typically induce undesirable or adverse side effects when administered in vivo. For example, biocompatible compounds may not induce side effects such as significant inflammation and/or acute rejection. It will be recognized that "biocompatibility" is a relative term, and some side effects can be expected even for some compounds that are biocompatible. In some embodiments, a biocompatible compounds does not induce irreversible side effects, and in some embodiments a compound is biocompatible if it does not induce long term side effects. One test to determine biocompatibility is to measure whether cells die upon being exposed a composition in vitro. For instance, a biocompatible compound may cause less than about 30%, 20%, 10%, or 5% cell death.

As stated above, embodiments of the present compounds can comprise an initiator and an active agent. The initiator is not particularly limited except that it must be a capable of forming a polymeric material with the active agent. In some embodiments the initiator is a monomer compound that can undergo a ring-opening polymerization process with the active agent. For instance, in some embodiments the initiator comprises one or more hydroxyl groups, and can be referred to herein as a hydroxylated monomer. In some embodiments it is preferable that the initiator have one group (e.g., hydroxyl group) that can initiate a ring-opening polymerization process, such as methoxypoly(ethylene glycol) (mPEG).

The type and size of the initiator can also be varied to tune the characteristics of the resulting compound. In some embodiments the initiator and/or the active agent has a hydrophobic character or a hydrophilic character. In a specific embodiments comprising a mPEG initiator, the initiator has a hydrophilic character. Thus, by tuning the relative concentration and/or size of the mPEG initiator, the resulting compound can be imparted with a relatively more hydrophobic or hydrophilic character.

The hydrophilic and hydrophobic characteristics of a compound can be tuned to, among other things, adjust the degradation rates of a compound. As described herein, some embodiments of compounds degrade via hydrolysis. Thus, for such embodiments, the degradation of the compound can increase as the hydrophilic character of the compound increases. In other words, hydrophilic compounds that more easily attract and absorb water permit can permit a greater degree of hydrolysis relative to more hydrophobic compounds that repel or at least to not permit water to contact the compound as easily. For instance, in some embodiments the relative concentration and/or molecular weight of a hydrophilic mPEG initiator can be increased in a compound to increase the hydrophilicity and relative degradation rate of the compound via hydrolysis.

The active agent to be used in embodiments of the presently-disclosed subject matter is also not particularly limited so long as it is capable of forming a polymeric material with the initiator. In this regard, the term "active agent" is used herein to refer to compounds or entities that alter, promote, speed, prolong, inhibit, activate, or otherwise affect biological or chemical events in a subject. Exemplary active agents include, but are not limited to, osteogenic agents, osteoinductive agents, and osteoconductive agents, anti-cancer agents, antibiotics, immunosuppressants, anti-viral agents, inhibitors, anti-histamines, anti-parasite agents, anti-protozoal agents, anti-fungal agents, analgesics, anti-inflammatory agents, anti-angiogenic factors, angiogenic factors, targeting agents, polypeptides, cells, polynucleotides, viruses, and vaccines. In some embodiments, the bioactive agent is a drug and/or a small molecule, such as a statin. Similar to the initiator, the active agent can comprise one or more groups that are suitable for undergoing a ring-opening polymerization process with the initiator.

In some embodiments the active agent and/or the initiator is selected to provide the compounds with one or more osteoconductive, osteoinductive, osteogenic, and osteointegrating properties. The term "osteoconductive" as used herein refers to the property of a compound or composition thereof to be receptive to the growth of new bone and stimulate bone tissue growth. The term "osteoinductive" as used herein refers to the property of a compound or composition thereof to promote bone growth in surrounding tissues by recruiting and differentiating mesenchymal stem cells into osteoblasts, which are cells that have the potential to form bone. The term "osteogenesis" as used herein refers to the property of a compound or composition thereof that can permit osteoprogenitor cells to remain on the compound or composition so that they may further proliferate, differentiate into characteristic bone cells, and adhere within the compound or composition. The term "osseointegration" as used herein refers to the property of a compound or composition thereof that can bind integratively to the surrounding bone tissue.

Exemplary groups include lactone groups. One active agent that can include lactone groups is simvastatin. Simvastatin is compound that can be used to reduce cholesterol and that also can possess osteogenic, anti-inflammatory, angiogenic, and other properties. In some implementations of the present compounds, simvastatin is administered as a prodrug in lactone form, and can then undergo hydrolysis by endogenous esterases to generate a hydroxyacid that acts as a 3-hydroxy-3-methylglutaryl coenzyme A (HMG-CoA) reductase inhibitor. By suppressing synthesis of mevalonate, farnesyl pyrophosphate, and geranylgeranyl pyrophosphate in a subject, simvastatin can be used to treat various diseases and conditions. For example, simvastatin can promote bone formation with increased bone morphogenic protein-2 (BMP-2) expression. It can also inhibit formation and activity of osteoclasts.

Further still, in some embodiments the compounds can act as and/or further comprise a targeting agent. The term "targeting agent" refers to a substance that can specifically bind another substance. In some embodiments a targeting agent specifically binds to particular proteins. Thus, targeting agents can include agents that specifically bind substances found at a wound site or on tissue to be treated.

Embodiments of the present compounds can comprise any molecular weight, and those of ordinary skill will appreciate that the size of the compounds can be modified depending on the subject to be treated, the wound to be treated, the desired compound properties, and the like. In some preferred embodiments the compounds include a linear or branched structure with a molecular weight of about 500 Da, 1,000 Da, 2,000 Da, 3,000 Da, 4,000 Da, 5,000 Da, 6,000 Da, 7,000 Da, 8,000 Da, 9,000 Da, or 10 kDa. Still further, in some embodiments the compounds can comprise a linear or branched structure with a molecular weight of about 15 kDa, 20 kDa, 25 kDa, 30 kDa, 35 kDa, 40 kDa, 45 kDa, 50 kDa, 55 kDa, 60 kDa, 65 kDa, 70 kDa, 75 kDa, 80 kDa, 85 kDa, 90 kDa, 95 kDa, or 100 kDa.

Furthermore, embodiments of the compounds can have any suitable molar ratio of initiator to the active agent. The molar ratio can be adjusted depending on the desired properties of the compound (e.g., hydrophilic vs. hydrophobic), the amount of active agent to be delivered, and the like. Exemplary compounds can have a molar ratio of active agent (e.g., simvastatin) to initiator (e.g., mPEG) of about 1:1 to about 100:1, including about 10:1, 20:1, 30:1, 40:1, 50:1, 60:1, 70:1, 80:1, 90:1, or 100:1.

The present compounds can form polymers having various configurations. In some embodiments the polymers are branched. In other embodiments the polymers are unbranched. Furthermore, in some embodiments the compounds are a copolymer comprising any suitable orientation of the initiator and the active agent. The term "copolymer" as used herein refers to a polymer formed of two or more different types of monomer units. Furthermore, in some embodiments the copolymer is an amphipathic block copolymer, wherein a "block" copolymer refers to a structure comprising one or more sub-combinations of constitutional or monomeric units. Thus, the term copolymer is inclusive of block copolymers. In some embodiments the copolymer is a diblock copolymer comprising two blocks. Exemplary diblock copolymers can include a block comprised of initiator monomers and a block comprised of active agent monomers. For example, in embodiments comprising an mPEG initiator and a simvastatin active agent, the compounds can include the following formula:

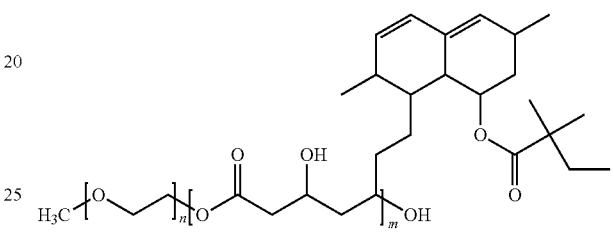

wherein n is about 1 to about 44, and m is about 1 to about 248. The compounds are not limited to diblock copolymers, and can include alternating copolymers and the like.

By virtue of directly binding the active agent to the initiator, the present compounds can form prodrugs of an active agent. The term "prodrug" is used herein to refer to an inactive or relatively less active form of an active agent that becomes active through one or more metabolic processes in a subject. For example, the present compounds can be administered to a subject as a prodrug that includes an initiator bound to an active agent, and, by virtue of being degraded by a metabolic process, the active agent is released from the compound in its active form. In some instances hydrolytic degradation of the present compounds converts the prodrug compounds from an inactive or relatively inactive form to an active form. In specific embodiments hydrolytic degradation releases biologically active simvastatin from a relatively inactive or less active mPEG-simvastatin copolymer.

The presently-disclosed subject matter also includes pharmaceutical compositions comprising the compounds described herein as well as a pharmaceutically acceptable carrier. The term "pharmaceutically acceptable carrier" refers to sterile aqueous or nonaqueous solutions, dispersions, suspensions or emulsions, as well as sterile powders for reconstitution into sterile solutions or dispersions just prior to use. The compositions can thus be in the form of a cream, paste, lotion, liquid, or the like.

Proper fluidity can be maintained, for example, by the use of coating materials such as lecithin, by the maintenance of the required particle size in the case of dispersions, and by the use of surfactants. These compositions can also contain adjuvants such as preservatives, wetting agents, emulsifying agents and dispersing agents. It can also be desirable to include isotonic agents such as sugars, sodium chloride and the like. The compositions can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose.

Suitable formulations include aqueous and non-aqueous sterile solutions that can contain antioxidants, buffers, bacteriostats, bactericidal antibiotics, and solutes that render the compositions isotonic with the bodily fluids of the intended recipient; and aqueous and non-aqueous sterile suspensions, which can include suspending agents and thickening agents.

The compositions can take such forms as suspensions, solutions, or emulsions in oily or aqueous vehicles, and can contain formulatory agents such as suspending, stabilizing and/or dispersing agents. Alternatively, the compositions can be in powder form for constitution with a suitable vehicle, e.g., sterile pyrogen-free water, before use.

The compositions can be presented in unit-dose or multi-dose containers, for example sealed ampoules and vials, and can be stored in a frozen or freeze-dried (lyophilized) condition requiring only the addition of sterile liquid carrier immediately prior to use.

The presently-disclosed subject matter further includes methods for making a compound. In some embodiments the methods comprise providing an initiator, mixing an active agent with the initiator to form a mixture, adding a catalyst to the mixture, and reacting the mixture to form a compound that includes the initiator and the active agent. The step of reacting the mixture to form the compound can comprise reacting the mixture via a ring-opening polymerization process.

With respect to the catalyst, various known catalysts may be utilized. Such catalysts include, but are not limited to, metallic catalysts, such as stannous octoate, aluminum isopropoxide, and yttrium isopropoxide, enzymatic catalysts, such as porcine pancreatic and *Candida Antarctica* lipases, and organic systems (organic catalysts), such as triazabicyclodecene and carboxylic acids with an alcohol. In some embodiments the mixture is provided with about 0.5 to 5 wt % of catalyst. In some embodiments the mixture for preparing the compositions includes about 0.1 to 5 wt % of the catalyst.

The reaction conditions as well as the reaction duration can be modified to tune the properties of the resulting compound. In some embodiments the step of reacting the mixture is performed at a predetermined temperature. The predetermined temperature can be, but is not limited to, temperatures of about 20° C., 30° C., 40° C., 50° C., 60° C., 70° C., 80° C., 90° C., 100° C., 110° C., 120° C., 130° C., 140° C., 150° C., 160° C., 170° C., 180° C., 190° C., 200° C., 210° C., 220° C., 230° C., 240° C., 250° C., or any temperatures therebetween. In some implementations, the molecular weight of the resulting compound increases as the reaction temperature increases.

Similarly, the reaction can be allowed to proceed for a predetermined time period. The time period can be about 1 to about 25 hours, including about 1, 2, 3, 4, 5, 6, 7, 8, 9, 10, 11, 12, 13, 14, 15, 16, 17, 18, 19, 20, 21, 22, 23, 24, or 25 hours. In some embodiments the polydispersity and/or the molecular weight of the resulting compounds increase as the reaction time is increased.

Further still, the presently-disclosed subject matter includes methods for treating a wound in a subject. In some embodiments the method comprises administering a composition to the wound, the composition including a compound that comprises an initiator and an active agent that is covalently bonded to the initiator through a ring-opening polymerization process. The various methods of treatment that are described herein can utilize any of the compounds that are described in this paper.

The terms "treatment" or "treating" refer to the medical management of a subject with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In some embodiments the term treatment refers to wound healing, tissue regeneration, or the like.

Also, the term "subject" is inclusive of both human and animal subjects. Thus, veterinary uses are provided in accordance with the presently disclosed subject matter and the presently-disclosed subject matter provides methods for preventing oxidative damage in mammals such as humans, as well as those mammals of importance due to being endangered, such as Siberian tigers; of economic importance, such as animals raised on farms for consumption by humans; and/or animals of social importance to humans, such as animals kept as pets or in zoos. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided is the treatment of livestock, including, but not limited to, domesticated swine, ruminants, ungulates, horses (including race horses), poultry, and the like.

In some embodiments of the present treatment methods, the step of administering the composition includes contacting the composition with the any surface that can support the composition. In some embodiments the surface includes a tissue wound surface. The term "tissue" is used herein to refer to a population of cells, generally consisting of cells of the same kind that perform the same or similar functions. In some embodiments tissue is part of a living organism, and in some embodiments tissue is tissue excised from a living organism or artificial tissue. In some embodiments tissue can be part of skin, bone, an organ, or the like.

Furthermore, the term "wound" is used herein to refer to any disease, condition, injury, defect, disorder, or the like present on any tissue that is in need of treatment. The wound itself can be a bone wound, a skin wound, some other tissue wound, or a combination thereof. In some embodiments a wound is bone (tissue) fracture. Thus, the presently-disclosed compounds can be administered to treat bone fractures that are the result of an injury, disease, disorder, or the like.

The composition can be administered with the compound in a prodrug form. Accordingly, as the composition that comprises the compounds degrades (e.g., via hydrolysis) within a subject, the active agent contained in the compound is released into the surrounding environment in its active form. The delivery of active agent that results from the degradation of a composition can be beneficial when treating a localized wound on a subject. Degradation of the composition can also provide a sustained and controllable release of active agent at a wound site.

Furthermore, the composition may be administered in several different forms. In some embodiments the composition is administered as a film. The film can be contacted with a wound on a subject. In other embodiments the composition is administered as nano- or microparticles, an oil-in-water emulsion, or as a three-dimensional scaffold. The scaffold itself can be porous or non-porous. Accordingly, the step of administering the composition, depending on the type of composition, the wound to be treated, and the like, can including injecting the composition on to a wound, contacting the composition on to a wound site, applying the composition as a paste or liquid on to a wound, or the like.

The present compositions and compounds can also be used as coating materials to coat medical devices, implants, or other devices configured to be implanted in or on a subject. The device can therefore include medical devices, biomaterials, or both. Devices that have been coated with the present compounds and compositions can provide a sustained and controlled delivery of active agent. The release of active agent from a coating can help ameliorate or accelerate the treatment of an existing wound. The release of active agent from a coating can also help mitigate adverse effects that may be caused by the implanted device.

EXAMPLES

The presently-disclosed subject matter is further illustrated by the following specific but non-limiting examples. The examples may include compilations of data that are representative of data gathered at various times during the course of development and experimentation related to the presently-disclosed subject matter. Furthermore, some of the examples described herein may be prophetic examples.

Example 1

This Example describes a process for making exemplary compounds comprising mPEG and a simvastatin active agent. This Example also describes procedures conducted to characterize the synthesized copolymers.

Stannous octoate was used for lactone polymerization given its relatively low cost, low toxicity, and high efficiency. With this reaction, the metal catalyst first forms a complex with the hydroxyl group of the initiator (i.e., mPEG) to form an alkoxide. The more reactive alkoxide then begins chain propagation by coordinating with the lactone ring of the monomer, followed by insertion of the ring into the alkoxide's metal-oxygen bond. Throughout the process, the alkoxide acts as a nucleophile by attacking the carbon of the ring's carbonyl group leading to cleavage of the acyl bond and extended chain formation. FIG. 1 shows a simplified representation of the exemplary simvastatin ROP reaction.

Methoxypoly(ethylene glycol) (mPEG) served as initiator in the ring-opening polymerization (ROP) reactions. Advantages of mPEG include that it comprises a single hydroxyl functionality and a boiling point suitable for the higher temperature reactions that can obtain higher molecular weight polymer.

Figure 2:
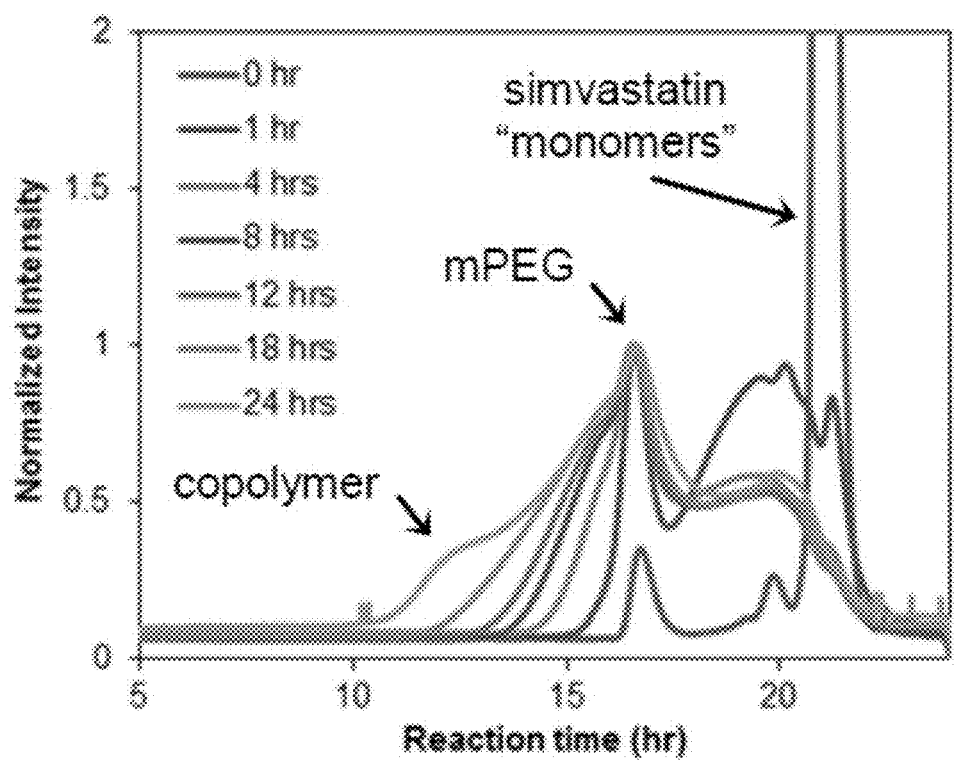
FIG. 2 includes a graph showing molecular weights of mPEG-polysimvastatin copolymers analyzed by gel permeation chromatography (GPC).
Figure 3:
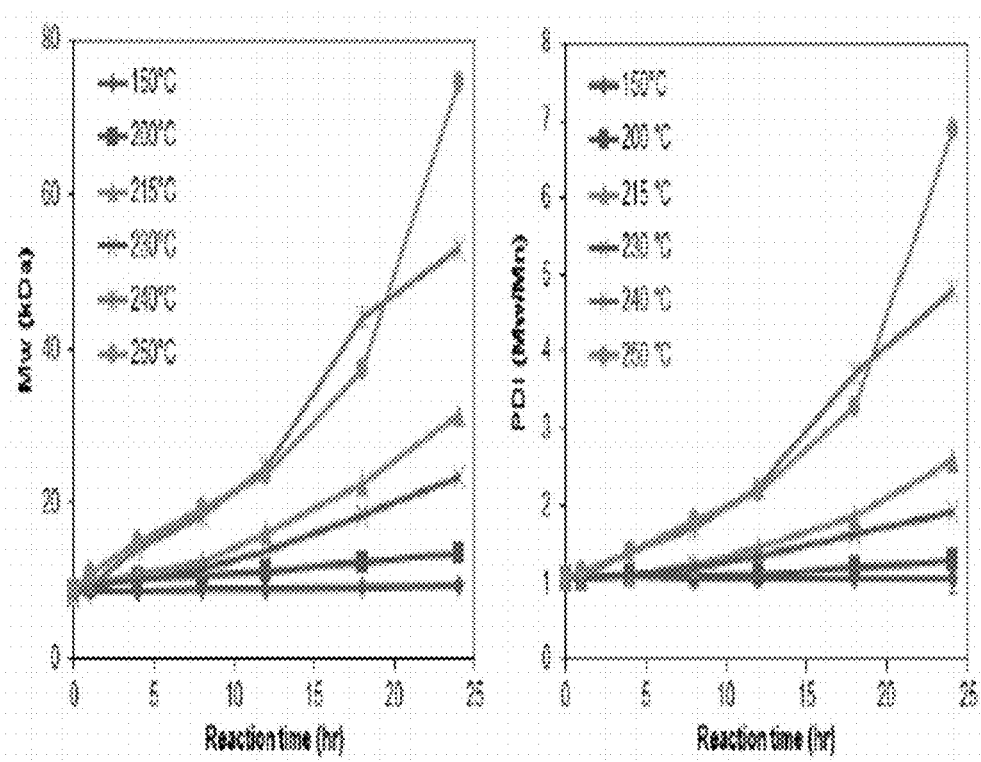
FIG. 3 includes a graph showing the molecular weights of mPEG-polysimvastatin copolymers that were synthesized at different temperatures as a function of time.
Figure 4:
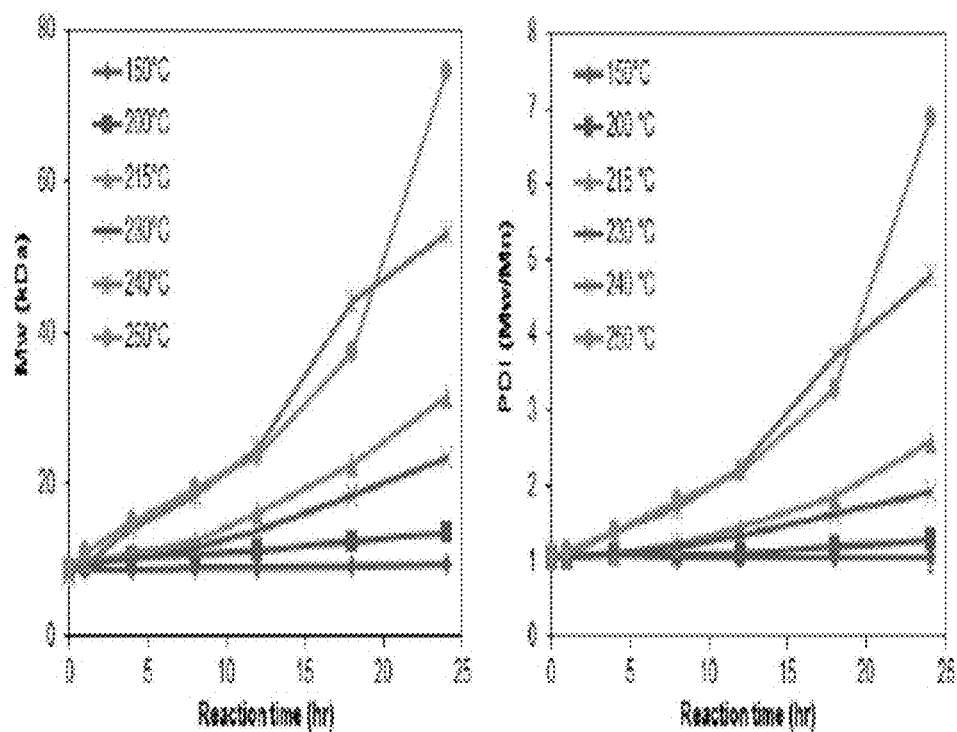
FIG. 4 includes a graph showing the polydispersity (PDI) of mPEG-polysimvastatin copolymers that were synthesized at different temperatures as a function of time.

The initial synthesis began with heating a 1:100 molar ratio of 5 kDa mPEG to simvastatin at 120° C. for 2 hours and then at 150° C. for 1 hour in a sand bath. After adding stannous octoate catalyst, reactions were allowed to proceed at different temperatures and for different times, with the reaction vessel continuously purged with nitrogen gas. The reaction product was precipitated in methylene chloride and diethyl ether followed by vacuum filtration. Molecular weights of the resulting polymers were analyzed by gel permeation chromatography (GPC) (FIG. 2). A distinct leftward shift can be seen as simvastatin "monomers" were consumed in the ROP reaction. FIGS. 3 and 4 shows quantification of the molecular weight and polydispersity of the polymers as a function of reaction temperature at 24 hours. In these procedures, polymers reaching nearly 80 kDa were synthesized.

Figure 5:
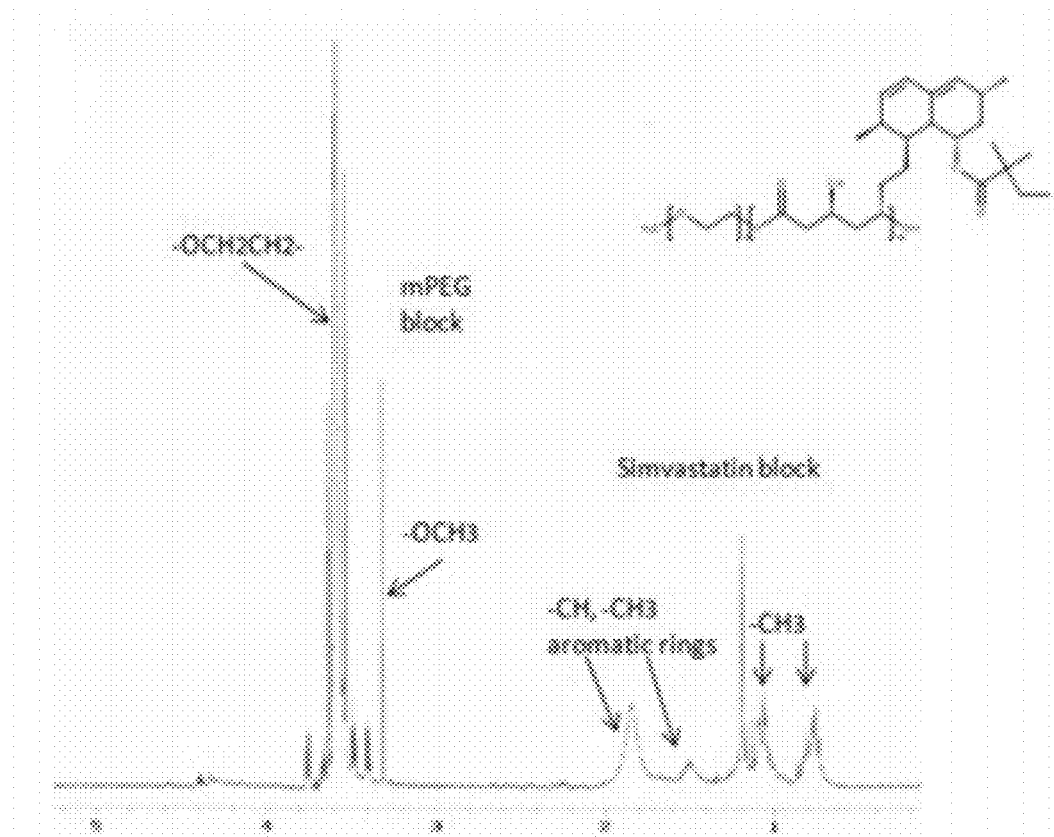
FIG. 5 includes a graph showing a $^1$H-NMR analysis of a mPEG-polysimvastatin copolymer.
Figure 6:
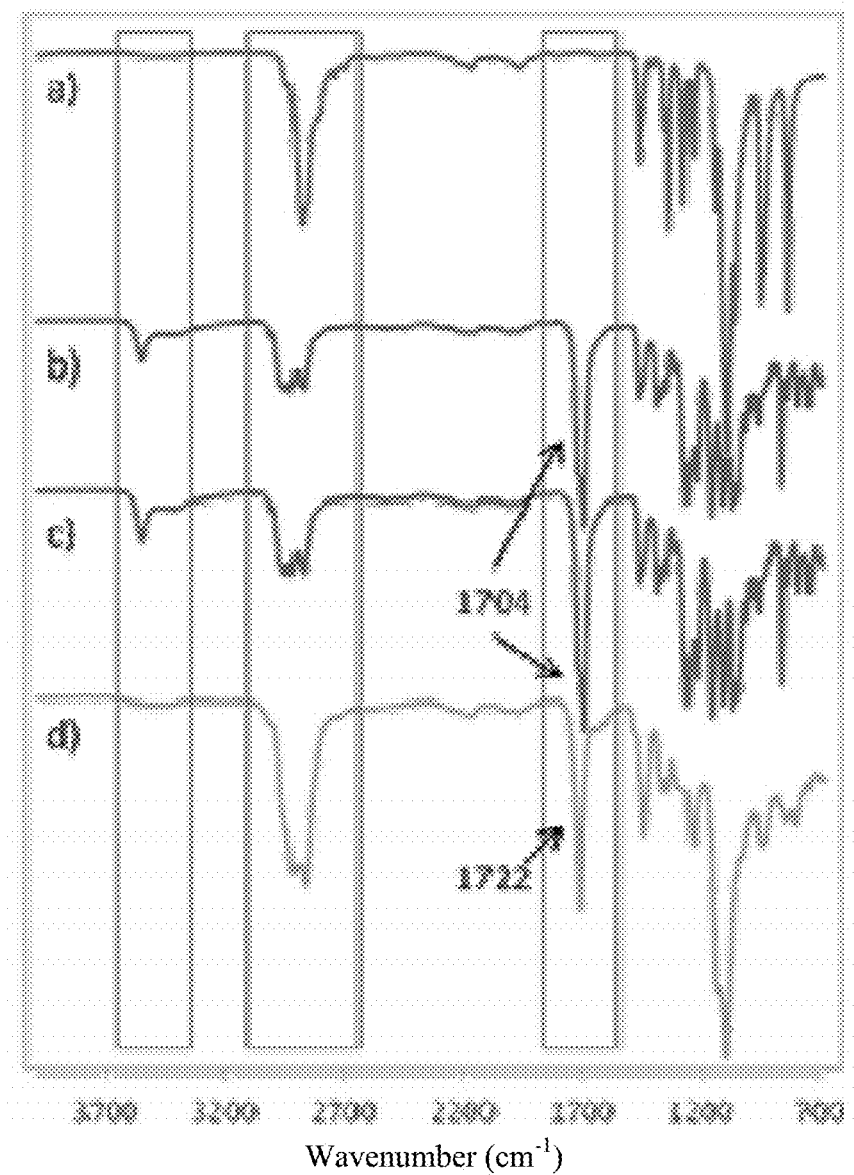
FIG. 6 includes a graph showing fourier transform infrared (FTIR) spectra of (a) mPEG, (b) simvastatin, (c) a simvastatin and mPEG blend (100:1), and (d) a purified mPEG-polysimvastatin copolymer.

Copolymer molecular weight, composition, and polydispersity were characterized by GPC, by preparing 5 to 10 mg/ml samples in tetrahydrofuran. Select samples were prepared in deuterated chloroform for supplementary structural analysis by $^1$H-NMR (University of Kentucky NMR Facility; Lexington, Ky.) (FIG. 5). Fourier transform infrared (FTIR) spectroscopy was also be used to evaluate the ratio of functional groups unique to individual block components of the copolymer and carbonyl peak shift analysis (FIG. 6).

Figure 7:
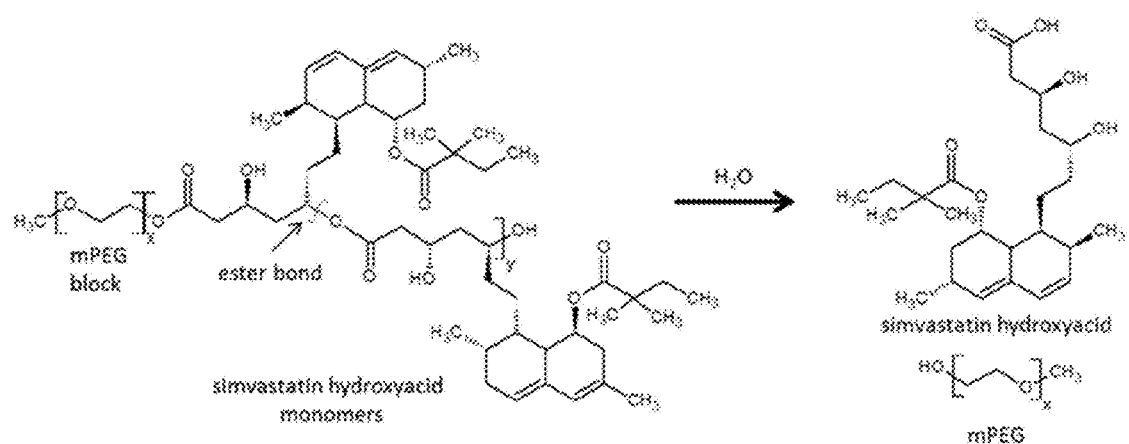
FIG. 7 includes a schematic diagram showing a hydrolytic degradation mechanism of a mPEG-poly(simvastatin) copolymer that results in the release of simvastatin molecules.
Figure 8:
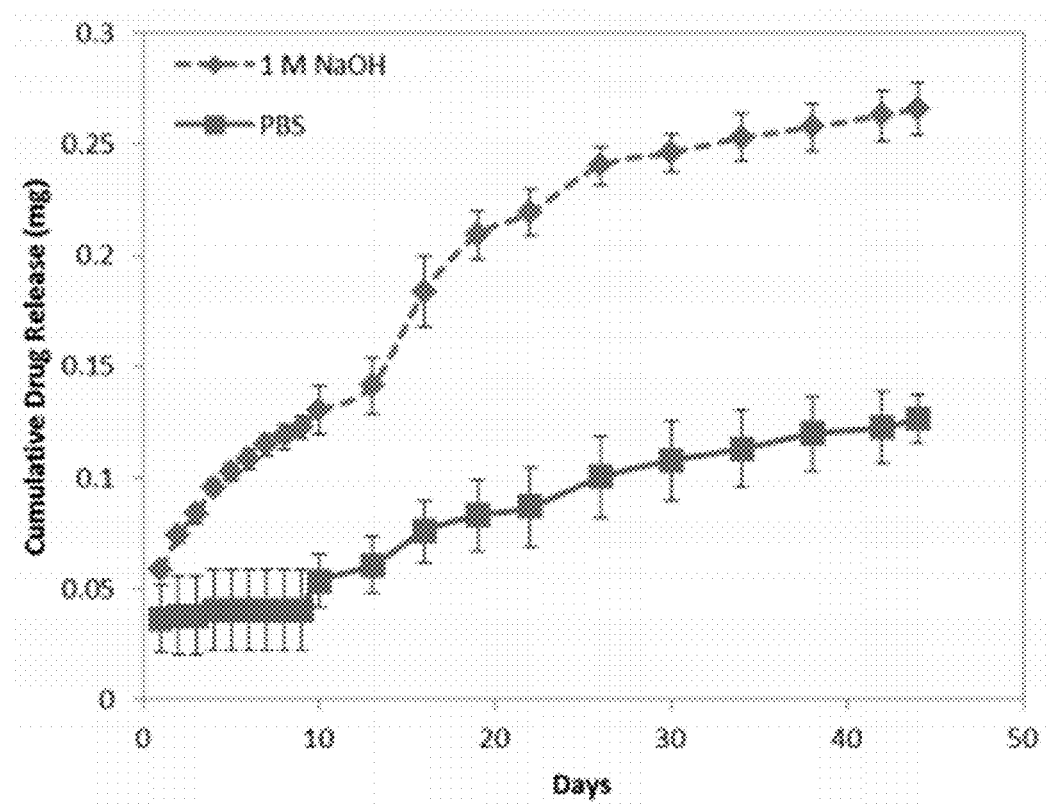
FIG. 8 includes a graph showing the change in absorbance of a degrading mPEG-simvastatin copolymer as a function of time in 1 M NaOH and in phosphate buffered saline (PBS).

Degradation kinetics with associated measurement of released simvastatin-containing molecules were assessed for films cast from the synthesized copolymers. Following incubation in a physiological buffer for increasing periods, mass loss was quantified. FIG. 7 shows a schematic of the hypothesized degradation mechanism. Degradation studies were conducted at both physiological (neutral) and alkaline (up to pH 12) conditions. Over a six week period, slow polymer degradation with associated slow release of simvastatin was observed (FIG. 8). For 16-18 mg samples, the cumulative drug amounts released were 108 and 266 µg in neutral (phosphate-buffered saline, PBS) and alkaline (NaOH) solutions, respectively. After an initial burst of 59 µg in 24 hr, a zero-order release rate was observed in NaOH with a constant of 7.4 µg·hr$^{-1}$ between 1 and 10 days. A first-order release rate followed with a constant of 21 d$^{-1}$ for the remainder of the degradation period. In PBS, after an initial burst of 37 µg in 24 hr, 2.5 µg was released during the following 8 days. A zero-order release constant of 2.1 µg·d$^{-1}$ was determined for the remainder of the degradation period. These degradation/release rates would yield formulations that can deliver the active agent for periods exceeding one year.

Example 2

This Example describes procedures to evaluate the efficacy of simvastatin-containing materials for treating bone wounds.

Simvastatin-based films are studied in a supracalvarial implantation model to assess osteogenic effects of simvastatin released from an erodible polymer system. This model enables testing of a material's ability to enhance formation of bone from existing bone surfaces outward (i.e., appositional bone formation). For this purpose, blank (no drug) and simvastatin-releasing implants were placed on the exposed calvarium, from which the periosteum containing osteoprogenitor cells had been displaced.

Figure 9:
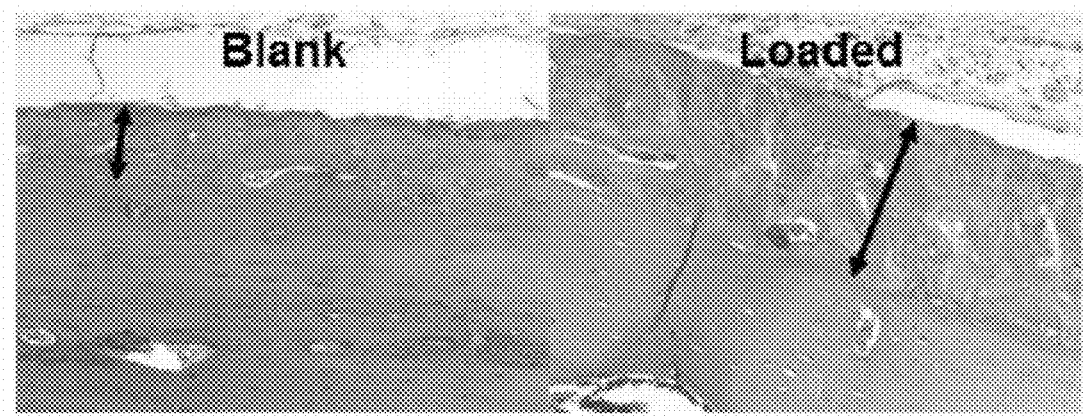
FIG. 9 includes images showing histological differences four weeks post-implantation in woven bone layers that were been treated with either no drug (blank) or with an embodiment of the present simvastatin-loaded compounds (loaded).
Figure 10:
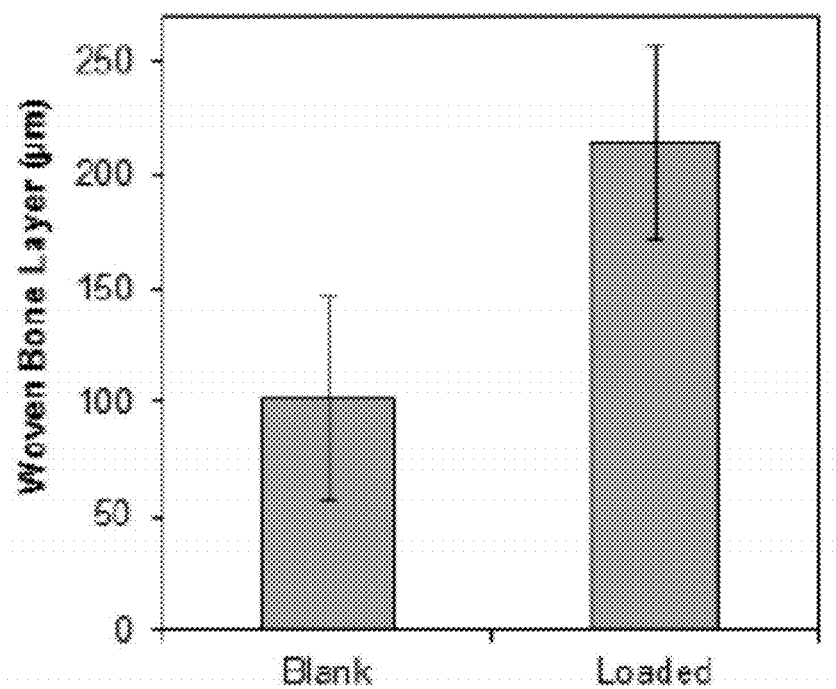
FIG. 10 includes a graph showing the thickness of woven bone layers formed over calvarias that were treated with either no drug (blank) or with an embodiment of the present simvastatin-loaded compounds (loaded).
Figure 11:
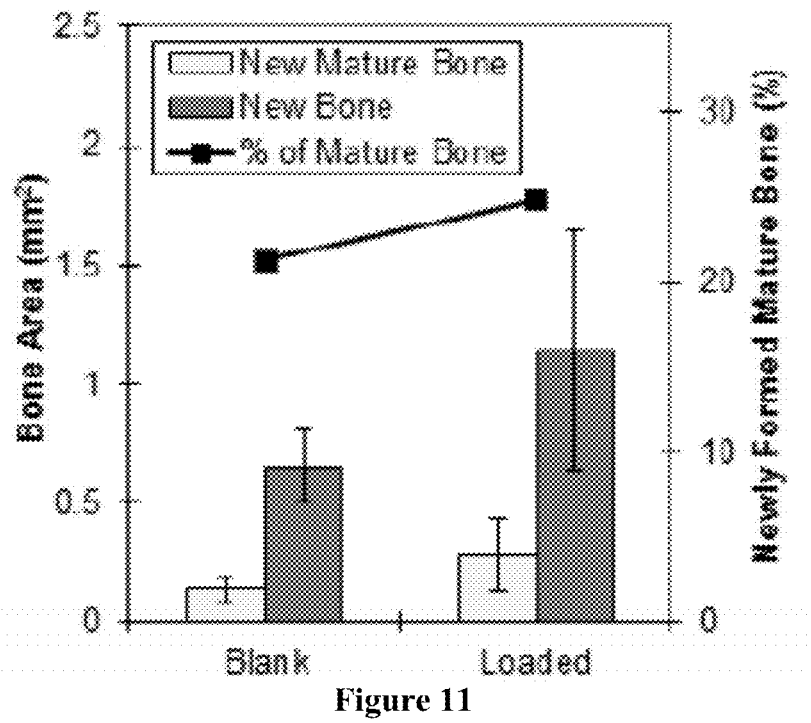
FIG. 11 includes a graph showing the new bone area and percentage of new formed mature bone formed over calvarias that were treated with either no drug (blank) or with an embodiment of the present simvastatin-loaded compounds (loaded).

Intimately opposed to the pre-existing lamellar bone of the calvarium was a layer of newly formed woven bone. The thickness of this layer depended on type of device. In the blank (no-drug control) animals, a low level of bone activity was observed, whereas simvastatin-loaded release devices stimulated formation of much more woven bone over the mature, lamellar calvarial bone (FIG. 9). Quantitatively, whereas disturbing the periosteum stimulated an average of 100 μm of woven bone formation, controlled release enhanced bone formation by over 110% (p<0.05) (FIG. 10). FIG. 11 shows the total area of new bone and the percentage of mature matrix relative to total bone. Simvastatin-loaded implants elicited 163% larger new bone area compared to controls, and the percentage of mature bone matrix (26%) was also higher than that of the controls (21%) (p<0.05).

Example 3

This Example describes another exemplary process for synthesizing an embodiment of the present compounds using triazabicyclodecene (TBD) as a catalyst. Unless stated otherwise, the same synthesis procedure described in Example 1 was followed.

Figure 12:
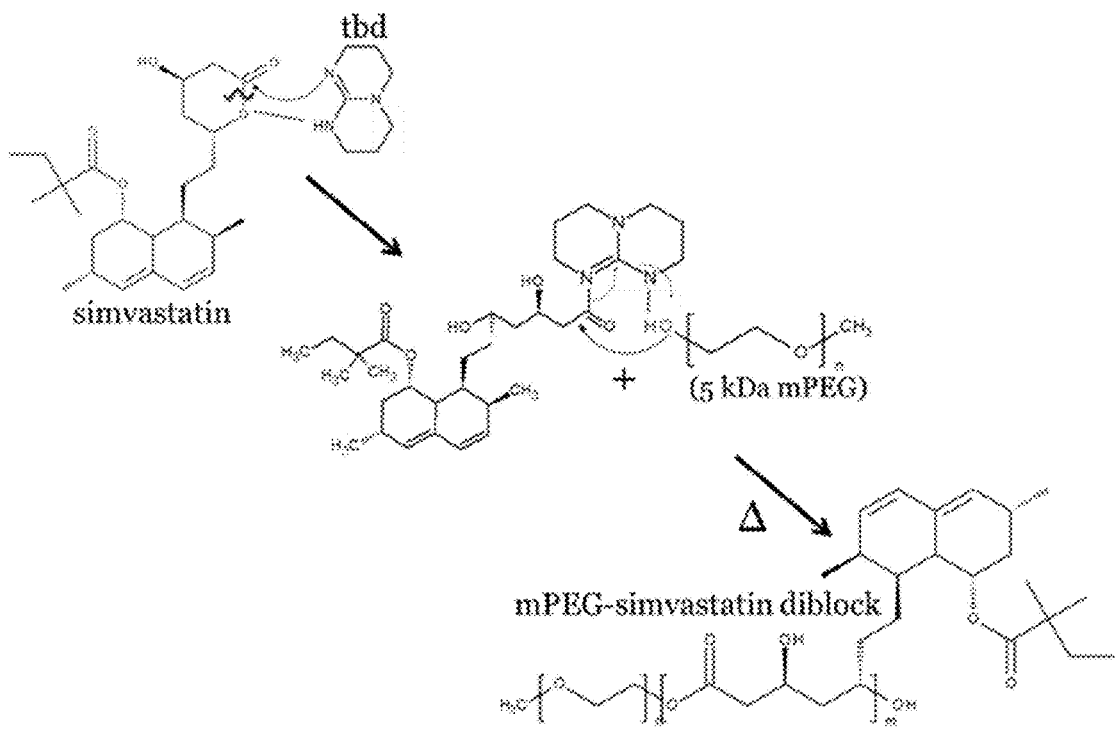
FIG. 12 includes a schematic diagram showing an anionic ring-opening polymerization reaction to form poly(ethylene glycol)-block-poly(simvastatin).

Triazabicyclodecene was selected was selected as the organic system to be used as a catalyst because of its efficient performance at ambient temperatures, ability to work without the need of a co-catalyst, and accessibility. The ring-opening polymerization mechanism of TBD is anionic (FIG. 12). Without being bound by theory, the amidine imine nitrogen of the nucleophilic catalyst attacks the carbonyl group on the lactone ring of simvastatin to form a temporary intermediate as the acyl bond is broken. The secondary amine within the catalyst activates or becomes attracted to the alcohols within the reaction mixture (i.e., both on mPEG and the propagating polysimvastatin block) to form the mPEG-poly(simvastatin) diblock copolymer through hydrogen bonding.

Figure 13A:
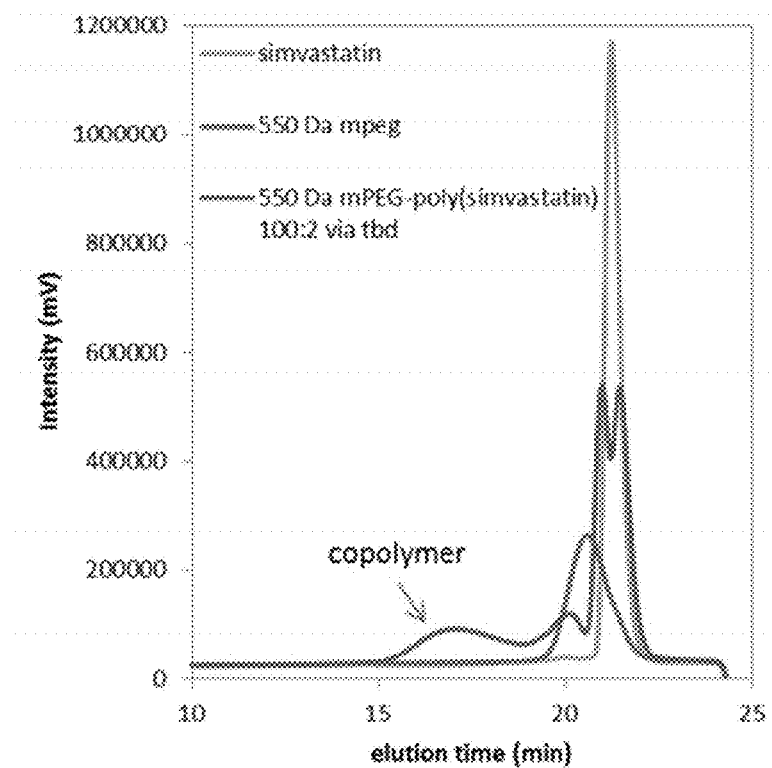
FIG. 13A includes a gel permeation chromatogram showing the peaks of an embodied compound synthesized with triazabicyclodecene (TBD) as well as the peaks of the initial reactants simvastatin and 550 Da mPEG.
Figure 13B:
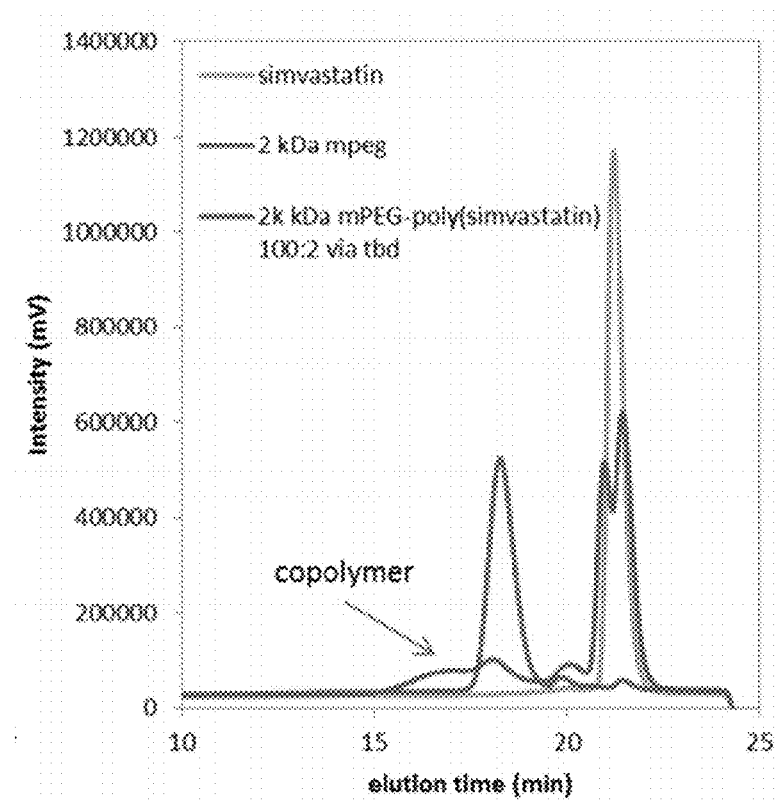
FIG. 13B includes a gel permeation chromatogram showing the peaks of an embodied compound synthesized with triazabicyclodecene (TBD) as well as the peaks of the initial reactants simvastatin and 2 kDa mPEG.
Figure 13C:
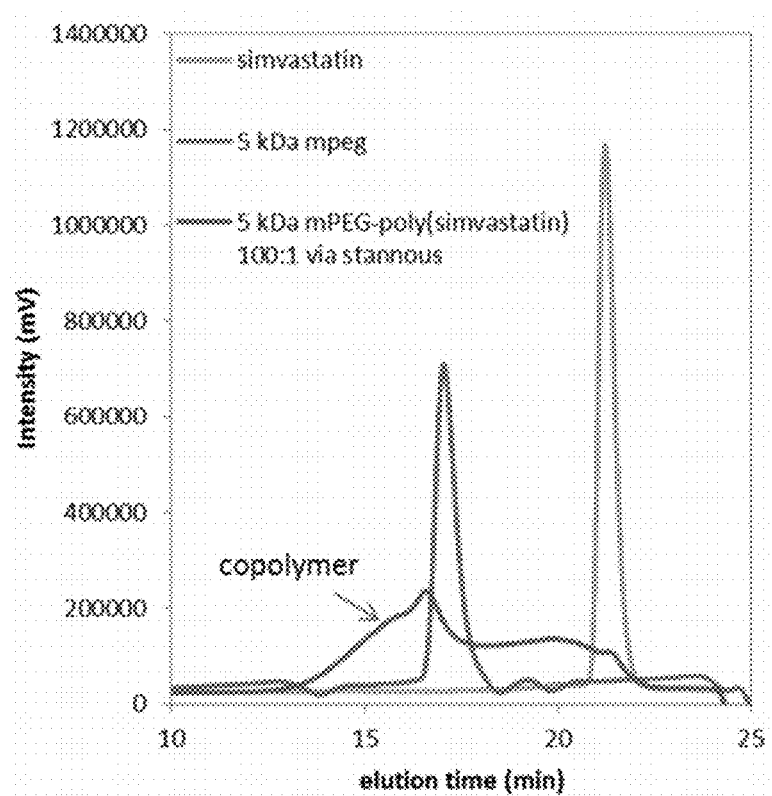
FIG. 13C includes a gel permeation chromatogram showing the peaks of an embodied compound synthesized with stannous octoate as well as the peaks of the initial reactants simvastatin and 5 kDa mPEG.

The results showed that TBD was able to form poly (ethylene glycol)-block-poly(simvastatin) with efficiency in polymerization using 550 Da and 2 kDa mPEG. A leftward shift of the polymer peak or shoulder is seen relative to the mPEG peaks, indicating an increase in overall molecular weight of the chains, and hence, growth of the poly(simvastatin) block (FIGS. 13A to 13C). Table 1 summarizes molecular weight and polydispersity results for the components and copolymers synthesized.

TABLE 1

MW comparisons of the diblock copolymers using 550 Da, 2 kDa, and 5 kDa mPEG, measured via GPC.

| Sample | $M_n$ (Da) | $M_w$ (Da) | $M_w/M_n$ | % of crude product |
|---|---|---|---|---|
| simvastatin | 300 | 320 | 1.0 | — |
| 550 Da mPEG | 470 | 560 | 1.2 | — |
| 2 kDa mPEG | 3200 | 3400 | 1.1 | — |
| 5 kDa mPEG | 8300 | 8800* | 1.1 | — |
| 550 Da mPEG-poly(simvastatin) 100:2 via TBD | 6500 | 10400 | 1.6 | 21 |
| 2k kDa mPEG-poly(simvastatin) 100:2 via TBD | 12700 | 15200 | 1.2 | 9.2 |
| 5 kDa mPEG-poly(simvastatin) 100:1 via stannous | 13100 | 29500 | 2.3 | 62 |

*The GPC molecular weight of mPEG registered higher than the expected value because its chemistry differs from the polystyrene standards used for calibration.

While the terms used herein are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although many methods, devices, and materials similar or equivalent to those described herein can be used in the practice or testing of the presently-disclosed subject matter, representative methods, devices, and materials are now described.

Following long-standing patent law convention, the terms "a", "an", and "the" refer to "one or more" when used in this application, including the claims. Thus, for example, reference to "a prodrug" includes a plurality of such prodrug, and so forth.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations in some embodiments of ±20%, in some embodiments of ±10%, in some embodiments of ±5%, in some embodiments of ±1%, in some embodiments of ±0.5%, and in some embodiments of ±0.1% from the specified amount, as such variations are appropriate to perform the disclosed method. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

Throughout this application, various publications are referenced. All such references, including the follow listed references, are incorporated herein by reference.

REFERENCES

1. Kopecek, J. (2013). Polymer-drug conjugates: Origins, progress to date and future directions, *Adv Drug Deliv Rev* 65:49-59.
2. Chang, K. Y. and Lee, Y. D. (2009). Ring-opening polymerization of epsilon-caprolactone initiated by the antitumor agent doxifluridine, *Acta Biomater* 5:1075-1081.
3. Hoffman, A. S. (2008). The origins and evolution of "controlled" drug delivery systems, *J Control Release* 132:153-163.
4. Erdmann, L., Macedo, B., and Uhrich, K. E. (2000). Degradable poly(anhydride ester) implants: effects of localized salicylic acid release on bone, *Biomaterials* 21:2507-2512.
5. Santo, V. E., Gomes, M., Mano, J., and Reis, R. L. (2012). Controlled release strategies for bone, cartilage and osteochondral engineering—Part I: Recapitulation of native tissue healing and variables for the design of delivery systems, *Tissue Eng Part B Rev.*
6. Santo, V. E., Gomes, M. E., Mano, J. F., and Reis, R. L. (2013). Controlled Release Strategies for Bone, Cartilage, and Osteochondral Engineering-Part II: Challenges on the Evolution from Single to Multiple Bioactive Factor Delivery, *Tissue Eng Part B Rev.*
7. Yu, N. Y., Schindeler, A., Little, D. G., and Ruys, A. J. (2010). Biodegradable poly(alpha-hydroxy acid) polymer scaffolds for bone tissue engineering, *J Biomed Mater Res B Appl Biomater* 93:285-295.
8. Ikada, Y. and Tsuji, H. (2000). Biodegradable polyesters for medical and ecological applications, *Macromol. Rapid Commun.* 21:117-132.
9. Gunatillake, P., Mayadunne, R., and Adhikari, R. (2006). Recent developments in biodegradable synthetic polymers, *Biotechnol Annu Rev* 12:301-347.
10. Yeo, Y. and Park, K. (2004). Control of encapsulation efficiency and initial burst in polymeric microparticle systems, *Arch Pharm Res* 27:1-12.
11. Mundargi, R. C., Babu, V. R., Rangaswamy, V., Patel, P., and Aminabhavi, T. M. (2008). Nano/micro technologies for delivering macromolecular therapeutics using poly(D, L-lactide-co-glycolide) and its derivatives, *J Control Release* 125:193-209.
12. Bouyer, E., Mekhloufi, G., Rosilio, V., Grossiord, J. L., and Agnely, F. (2012). Proteins, polysaccharides, and their complexes used as stabilizers for emulsions: alternatives to synthetic surfactants in the pharmaceutical field?, *Int J Pharm* 436:359-378.
13. Erdmann, L. and Uhrich, K. E. (2000). Synthesis and degradation characteristics of salicylic acid-derived poly (anhydride-esters), *Biomaterials* 21:1941-1946.
14. Schmeltzer, R. C. and Uhrich, K. E. (2006). Synthesis and characterization of antiseptic-based poly(anhydride-esters), *Polymer Bulletin* 57:281-291.
15. Rosario-Melendez, R., Harris, C. L., Delgado-Rivera, R., Yu, L., and Uhrich, K. E. (2012). PolyMorphine: an innovative biodegradable polymer drug for extended pain relief, *J Control Release* 162:538-544.
16. Todd, P. A. and Goa, K. L. (1990). Simvastatin. A review of its pharmacological properties and therapeutic potential in hypercholesterolaemia, *Drugs* 40:583-607.
17. Mundy, G., Garrett, R., Harris, S., Chan, J., Chen, D., Rossini, G., Boyce, B., Zhao, M., and Gutierrez, G. (1999). Stimulation of bone formation in vitro and in rodents by statins, *Science* 286:1946-1949.
18. Sugiyama, M., Kodama, T., Konishi, K., Abe, K., Asami, S., and Oikawa, S. (2000).
Compactin and simvastatin, but not pravastatin, induce bone morphogenetic protein-2 in human osteosarcoma cells, *Biochem. Biophys. Res. Commun.* 271:688-692.
19. Garrett, I. R., Gutierrez, G., and Mundy, G. R. (2001). Statins and bone formation, *Curr. Pharm. Des.* 7:715-736.
20. Maeda, T., Matsunuma, A., Kurahashi, I., Yanagawa, T., Yoshida, H., and Horiuchi, N. (2004). Induction of osteoblast differentiation indices by statins in MC3T3-E1 cells, *J. Cell Biochem.* 92:458-471.
21. Parhami, F., Mody, N., Gharavi, N., Ballard, A. J., Tintut, Y., and Demer, L. L. (2002). Role of the cholesterol biosynthetic pathway in osteoblastic differentiation of marrow stromal cells, *J. Bone Miner. Res.* 17:1997-2003.
22. Grasser, W. A., Baumann, A. P., Petras, S. F., Harwood, H. J., Jr., Devalaraja, R.,
Renkiewicz, R., Baragi, V., Thompson, D. D., and Paraklar, V. M. (2003). Regulation of osteoclast differentiation by statins, *J. Musculoskelet. Neuronal Interact.* 3:53-62.
23. Staal, A., Frith, J. C., French, M. H., Swartz, J., Gungor, T., Harrity, T. W., Tamasi, J., Rogers, M. J., and Feyen, J. H. (2003). The ability of statins to inhibit bone resorption is directly related to their inhibitory effect on HMG-CoA reductase activity, *J. Bone Miner. Res.* 18:88-96.
24. Hughes, A., Rogers, M. J., Idris, A. I., and Crockett, J. C. (2007). A Comparison between the Effects of Hydrophobic and Hydrophilic Statins on Osteoclast Function In Vitro and Ovariectomy-Induced Bone Loss In Vivo, *Calc Tissue Int.* 81:403-413.
25. Diomede, L., Albani, D., Sottocorno, M., Donati, M. B., Bianchi, M., Fruscella, P., and Salmona, M. (2001). In vivo anti-inflammatory effect of statins is mediated by nonsterol mevalonate products, *Arterioscler Thromb Vasc Biol* 21:1327-1332.
26. Elewa, H. F., El-Remessy, A. B., Somanath, P. R., and Fagan, S. C. (2010). Diverse effects of statins on angiogenesis: new therapeutic avenues, *Pharmacotherapy* 30:169-176.
27. Adam, O. and Laufs, U. (2008). Antioxidative effects of statins, *Arch Toxicol* 82:885-892.
28. Mermis, J. D. and Simpson, S. Q. (2012). HMG-CoA Reductase Inhibitors for Prevention and Treatment of Severe Sepsis, *Curr Infect Dis Rep* 14:484-492.
29. Bjorkhem-Bergman, L., Ekstrom, L., and Eriksson, L. C. (2012). Review: Exploring anticarcinogenic agents in a rat hepatocarcinogenesis model—focus on selenium and statins, *In Vivo* 26:527-535.
30. Labet, M. and Thielemans, W. (2009). Synthesis of polycaprolactone: a review, *Chem Soc Rev* 38:3484-3504.
31. Storey, R. F. and Sherman, J. W. (2002). Kinetics and mechanism of the stannous octoate-catalyzed bulk polymerization of epsilon-caprolactone, *Macromolecules* 35:1504-1512.
32. Odian, G. G. (2004). *Principles of Polymerization.* Hoboken, N.J.: Wiley-Interscience.
33. Kricheldorf, H. R., Kreisersaunders, I., and Boettcher, C. (1995). *Polylactones* 0.31. Sn(li)Octoate-Initiated Polymerization of L-Lactide—a Mechanistic Study, *Polymer* 36:1253-1259.
34. Wattamwar, P. P., Biswal, D., Cochran, D. B., Lyvers, A. C., Eitel, R. E., Anderson, K. W., Hilt, J. Z., and Dziubla, T. D. (2012). Synthesis and characterization of poly (antioxidant beta-amino esters) for controlled release of polyphenolic antioxidants, *Acta Biomater* 8:2529-2537.
35. Wattamwar, P. P., Hardas, S. S., Butterfield, D. A., Anderson, K. W., and Dziubla, T. D. (2011). Tuning of the pro-oxidant and antioxidant activity of trolox through the controlled release from biodegradable poly(trolox ester) polymers, *J Biomed Mater Res A* 99:184-191.
36. Pearce, A. I., Richards, R. G., Milz, S., Schneider, E., and Pearce, S. G. (2007). Animal models for implant biomaterial research in bone: a review, *Eur Cell Mater* 13:1-10.
37. Muschler, G. F., Raut, V. P., Patterson, T. E., Wenke, J. C., and Hollinger, J. O. (2010). The design and use of animal models for translational research in bone tissue engineering and regenerative medicine, *Tissue Eng Part B Rev* 16:123-145.
38. Mills, L. A. and Simpson, A. H. (2012). In vivo models of bone repair, *J Bone Joint Surg Br* 94:865-874.
39. Jeon, J. H., Piepgrass, W. T., Lin, Y. L., Thomas, M. V., and Puleo, D. A. (2008). Localized intermittent delivery of simvastatin hydroxyacid stimulates bone formation in rats, *J Periodontol* 79:1457-1464.
40. Jahangir, A. A., Numley, R. M., Mehta, S., and Sharan, A. (2008). Bone-graft substitutes in orthopaedic surgery, in AAOS Now, American Academy of Orthopaedic Surgeons, http://www.aaos.oro/news/aaosnow/jan08/reimbursement2.asp.

41. Population Division (2000). National population projections, NP-D1-B, U.S. Census Bureau, http://www.census-siov/population/www/prolections/natdet.html.
42. TransWorldNews (2012). Bone Graft Substitutes Market to Reach $3.3 billion by 2017, http://transworld news-.com/1231994/a70079/retoort-bone-q raft-substitutes-market-to-reach-3-point-3-billion-bv-2017.
43. Greenwald, A. S., Boden, S. D., Barrack, R I., Bostrom, M. P. G., Goldberg, V. M., Yaszemski, and Heim, C. S. (2010). The evolving role of bone-graft substitutes, American Academy of Orthopaedic Surgeons, http://orl-inc.com/aaospublications/2010/BoneGraft Substitutes2010.pdf.
44. Kolk, A., Handschel, J., Drescher, W., Rothamel, D., Kloss, F., Blessmann, M., Heiland, M., Wolff, K. D., and Smeets, R. (2012). Current trends and future perspectives of bone substitute materials—from space holders to innovative biomaterials, J Craniomaxillofac Surg 40:706-718.
45. Carragee, E. J., Ghanayem, A. J., Weiner, B. K., Rothman, D. J., and Bono, C. M. (2011). A challenge to integrity in spine publications: years of living dangerously with the promotion of bone growth factors, Spine J 11:463-468.
46. Ikada, Y. and Tsuji, H. (2000). Biodegradable polyesters for medical and ecological applications, Macromol. Rapid Commun. 21:117-132.
47. Ravi, N., Gupta, G., Milbrandt, T. A., and Puleo, D. A. (2012). Porous PLGA scaffolds for controlled release of naked and polyetheneimine-complexed DNA, Biomed Mater 7:055007.
48. Sundararaj, S. K., Cieply, R. D., Gupta, G., Milbrandt, T. A., and Puleo, D. A. (2012). Treatment of growth plate injury using IGF-I-loaded PLGA scaffolds, J Tissue Eng Regen Med.
49. Mikos, A. G., Thorsen, A. J., Czerwonka, L. A., Bao, Y., Langer, R., Winslow, D. N., and Vacanti, J. P. (1994). Preparation and characterization of poly(L-lactic acid) foams, Polymer 35:1068-1077.
50. Sargeant, T. D., Guler, M. O., Oppenheimer, S. M., Mata, A., Satcher, R. L., Dunand, D. C., and Stupp, S. I. (2008). Hybrid bone implants: self-assembly of peptide amphiphile nanofibers within porous titanium, Biomaterials 29:161-171.
51. Li, B., Yoshii, T., Hafeman, A. E., Nyman, J. S., Wenke, J. C., and Guelcher, S. A. (2009). The effects of rhBMP-2 released from biodegradable polyurethane/microsphere composite scaffolds on new bone formation in rat femora, Biomaterials 30:6768-6779.
52. Raiche, A. T. and Puleo, D. A. (2001). Triphasic release model for multilayered gelatin coatings that can recreate growth factor profiles during wound healing, J Drug Target 9:449-460.
53. Global Strategies to reduce the health-care burden of craniofacial anomalies: Report of WHO meetings on international collaborative research on craniofacial anomalies, World Health Organization, Geneva, Switzerland, 2002.
54. Global Registry and Database for Craniofacial Anomalies, World Health Organization, 2003, 15-33.
55. Scheller E L and Krebsbach P H, Gene Therapy: Design and Prospects for Craniofacial Regeneration, J Dent Res. 2009 (7): 585-596.
56. Dimitriou et al. Bone Regeneration: Current Concepts and Future Directions, BMC Medicine (9)201, 6675.
57. Bostrom MPG and Seigerman D A, The Clinical Use of Allografts, Demineralized Bone Matrices, Synthetic Bone Graft Substitutes and Osteoinductive Growth Factors: A Survey Study. HSS J. (1) 2005, 9-18.
58. Giannoudis P V, Dinopoulos H, Tsiridis E, Bone substitutes: An update. Injury (36)2005, S20-S27.
59. Porter J R, Ruckh T T, and Popat K C. Bone Tissue Engineering: A Review in Bone Biomimetics and Drug Delivery Strategies. Biotechnol. Prog., (25) 2009, 1539-1560.
60. Mourino V and Boccaccini A R. Bone tissue engineering therapeutics:controlled drug delivery in three-dimensional scaffolds. Journal of the Royal Society, Interface (7)2010, 209-227.
61. Rezwan K et al., Biodegradable and bioactive porous polymer/inorganic composite scaffolds for bone tissue engineering, Biomaterials (27)2006, 3413-3431.
62. Gunatillake P A and Adhikari R. Biodegradable Synthetic Polymers for Tissue Engineering, European cells and materials (5) 2003, 1-16.
63. Yoshito I and Tsujh H, Biodegradable polyesters for medical and ecological applications, Macromolecular Rapid Communications (2)2002, 1022-1336.
64. Middleton J C and Tipton A J. Synthetic biodegradable polymers as orthopedic devices, Biomaterials (21) 2000, 2335-2346.
65. Bergsma J E, Debruijn W C, Rozema F R et. al., Late degradation tissue response to poly(I-lactide) bone plates and screws, Biomaterials, (16)1995, 25-31.
66. Cleek R L et al., Microparticles of poly(dl-lactic-co-glycolic acid)/poly(ethylene glycol) blends for controlled drug delivery, Journal of Controlled Release (48), 259-268.
67. Joshi H N, Recent Advances in Drug Delivery Systems, Pharmaceutical Technology 1988.
68. Banerjee S S, Poly(ethylene glycol)-Prodrug Conjugates:Concept, Design, and Applications, Journal of Drug Delivery 2012.
69. Carbone A L and Uhrich K E, Design and Synthesis of Fast-Degrading Poly(anhydride-esters), Macrornol Rapid Commun (30) 2009: 1021-1026.
70. Wattamwar P P et al., Antioxidant Activity of Degradable Polymer Poly(trolox-ester) to Suppress Oxidative Stress Injury in the Cells, Advanced Functional Materials (20) 2010, 147-154.
71. Dhandayuthapani B et al., Polymeric Scaffolds in Tissue Engineering Application: A Review, International Journal of Polymer Science (2011) 2011, 1-19.
72. Causa F, Netti P A, Ambrosio L et al., Poly-E-caprolactone/hydroxyapatite composites for bone regeneration: In vitro characterization and human osteoblast response. Journal of Biomedical Materials Research (76A) 2006, 151-162.
73. Zhang R and Ma P X, Poly(a-hydroxyl acids)/hydroxyapatite porous composites for bone tissue engineering. I. Preparation and morphology. J Biomed Mater Res, (44) 1999, 446-455.
74. Wong R W and Rable A B, Statin-Induced osteogenesis uses in orthodontics; a scientific review, World Journal of Orthodontics (7)2006, 35-40.
75. Jeon J H, M V Thomas, and Puleo D A, Bioerodible devices for intermittent release of simvastatin acid. Int J Pharm. 340(1-2) 2007, 6-12.
76. Xie X and Tang Y, Efficient Synthesis of Simvastatin by Use of Whole-Cell Biocatalysis, Applied and Environmental Microbiology (2007), 2054-2060.
77. Istvan E S et al., Structural Mechanism for Statin Inhibition of HMG-CoA Reductase, Science (292) 2001, 1160-1164.

78. Sparrow C P et al., Simvastatin Has Anti-Inflammatory and Anti-atherosclerotic Activities Independent of Plasma Cholesterol Lowering, Arteriosclerosis Thrombosis and Vascular Biology (21)2001, 115-121.
79. Chen P et. al., Simvastatin promotes osteoblast viability and differentiation via Ras/Smad/Erk/BMP-2 signaling pathway, Nutrition Research (30) 2010, 191-199.
80. Park J B, Use of simvastatin in bone regeneration, Med Oral Patol Oral Cir Bucal. (14) 2009, 485-488.
81. Uzzan B, Effects of statins on bone mineral density: A meta-analysis of clinical studies, Bone (40) 2007 [31] Prueksaritanont et al., In vitro metabolism of simvastatin in humans identification of metabolizing enzymes and effect of the drug on hepatic p450s, American Society for Pharmacology and Experimental Therapeutics (25)1997, 1191-1199.
82. Dziubla T D, Karim A and Muzykantov V R, Polymer nanocarriers protecting active enzyme cargo against proteolysis, Journal of Controlled Release. (102)2005, 427-39.
83. Kaesemeyer W H, Caldwell R B, Huang J, Caldwell R W. Pravastatin sodium activates endothelial nitric oxide synthase independent of its cholesterol-lowering actions. J Am Coll Cardiol (33)1999, 234-241.
84. Gross R A Ganesh M., and Lu W, Enzyme catalysis breathes new life into polyester condensation polymerizations, Trends in Biotechnology (28)2010, 435-443.
85. Muthu M S, Nanoparticles based on PLGA and its co-polymer: An overview, Asian Journal of Pharmaceutics 2009.
86. Athanasiou K A, Niederauer G G, Agrawal C M, Sterilization, Toxicity, Biocompatibility and Clinical Applications of Polylactide acid/Polyglycolic acid copolymers, Biomaterials, (17)1996, 93-102.
87. Kalyanasundaram K and Thomas J K, Environmental Effects on Vibronic Band Intensities in Pyrene Monomer Fluorescence and Their Application in Studies of Micellar Systems, Journal of the American Chemical Society, (99)1977, 2039-2044.
88. Mikos A G et al. Mechanical Properties of a Biodegradable Bone Regeneration Scaffold, Journal of Biomechanical Engineering (122) 2000, 286-287.
89. Azevedo H S and Reis R L, Biodegradable Systems in Tissue Engineering and Regenerative Medicine, CRC Press LLC, 2005, 177-349.
90. Hollister S J et al., Engineering Craniofacial Scaffolds, Orthod Craniofacial (8) 2005, 162-173.
91. Muratov A and Baulin V A, Degradation versus self-assembly of block copolymer micelles, Langmuir (28) 2012, 3071-3076.
92. Hermanson G T, Bioconjugate Techniques, Academic Press 1996, 606-608.
93. Stein D, Lee Y, Schmid M J, et al., Local Simvastatin Effects on Mandibular Bone Growth and Inflammation, Journal of Periodontology 2005, 1861-1870.
94. Yang F et al. Simvastatin-loaded porous implant surfaces stimulate preosteoblasts differentiation: an in vitro study, 000E, 2011, 551-556.
95. Calixto J C, The influence of local administration of simvastatin in calvarial bone healing in rats, Journal of Cranio-Maxillofacial Surgery, (39) 2011, 215-220.
96. Zong C et al., Reconstruction of Rat Calvarial Defects with Human Mesenchymal Stem Cells and Osteoblast-like Cells in Poly-Glycolic-co-Lactic acid scaffolds, European Cells and Materials (20) 2010, 109-120.

What is claimed is:

1. The compound having the formula:

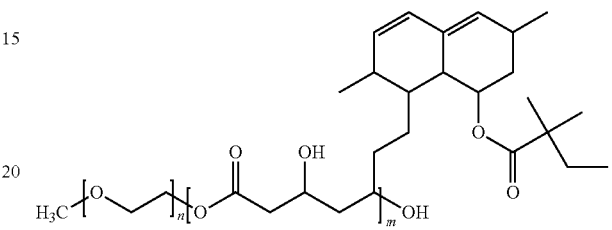

wherein:
n is about 1 to about 44; and
m is about 1 to about 258.

2. The compound of claim 1, further comprising a targeting agent.

3. The compound of claim 1, wherein the compound includes a linear or branched structure with a molecular weight of about 500 Da to about 80 kDa.

4. The compound of claim 1, wherein a molar ratio of the initiator to the active agent is about 1:1 to about 1:100.

5. A method for making the compound of claim 1, comprising:
providing methoxypoly(ethylene glycol);
mixing imvastatin with the methoxypoly(ethylene glycol) to form a mixture;
adding a catalyst to the mixture; and
reacting the mixture via a ring-opening polymerization process to form the compound of claim 1.

6. The method of claim 5, wherein a molar ratio of the methoxypoly(ethylene glycol) to simvastatin is about 1:1 to about 1:100.

7. The method of claim 5, wherein the catalyst is selected from a metallic catalyst, an enzymatic catalyst, an organic catalyst, and combinations thereof.

8. A method for treating a wound in a subject, comprising:
administering the composition of claim 1 to the wound.

9. The method of claim 8, wherein the step of administering a composition includes contacting the wound with the composition.

10. The method of claim 8, wherein the wound is a bone wound, a skin wound, or a combination thereof.

* * * * *

UNITED STATES PATENT AND TRADEMARK OFFICE
CERTIFICATE OF CORRECTION

PATENT NO. : 9,433,638 B1  
APPLICATION NO. : 14/505381  
DATED : September 6, 2016  
INVENTOR(S) : David Puleo et al.

It is certified that error appears in the above-identified patent and that said Letters Patent is hereby corrected as shown below:

In the Claims,

Claim 5, col. 20, line 37, change "imvastatin" to "simvastatin"

Signed and Sealed this
First Day of November, 2016

Michelle K. Lee
*Director of the United States Patent and Trademark Office*